United States Patent [19]

Duinker

[11] 4,200,931
[45] Apr. 29, 1980

[54] SIGNAL PROCESSING SYSTEM
[75] Inventor: Simon Duinker, Bloemendaal, Netherlands
[73] Assignee: N.V. Optische Industrie "De Oude Delft", Delft, Netherlands
[21] Appl. No.: 829,055
[22] Filed: Aug. 30, 1977
[30] Foreign Application Priority Data
Sep. 8, 1976 [NL] Netherlands ................. 7609963
[51] Int. Cl.² ........................................ G01N 21/00
[52] U.S. Cl. ............................... 364/414; 250/445 T
[58] Field of Search ............... 364/414, 571, 604, 819, 364/822, 728; 250/445 R, 445 T, 345, 363 S

[56] References Cited
U.S. PATENT DOCUMENTS

| 3,809,873 | 5/1974 | Klahr | 364/822 |
|---|---|---|---|
| 4,066,902 | 1/1978 | LeMay | 250/363 S |
| 4,068,306 | 2/1978 | Chen et al. | 364/414 |
| 4,075,483 | 2/1978 | Tancrell et al. | 250/363 S |

OTHER PUBLICATIONS

Sterling et al.; Dynamic Display of Radiotherapy Plans Using Computer-Produced Films; Work in Progress, Radiology, vol. 7, pp. 689-691, Jun. 1973.

Primary Examiner—Errol A. Krass
Attorney, Agent, or Firm—O'Brien & Marks

[57] ABSTRACT

A system for synthesizing a radiation divergence correcting operation and a deconvolution operation, for use in a tomographic apparatus, comprising optical storing means for a collection of primary signal profiles in analog form obtained by exposing a subject to a substantially flat, and diverging beam of penetrating radiation from different directions, and collecting the radiation transmission at positions, corresponding to the associated angles of incident radiation; projecting means for sequentially projecting primary signal profiles in an annular region of a memory device; and read out means including a rotating filter for sequentially and in correspondence to a correcting deconvolution function reading out simultaneously all information elements as are stored in different ones of said primary signal profiles and as are included in a particular one of said trajectories.

6 Claims, 5 Drawing Figures

SIGNAL PROCESSING SYSTEM

This invention relates to a mechanical-electrical signal processing system for use in analog tomographic systems. Analog systems, in contrast with computerized tomographic systems, employ analog techniques instead of digital techniques to form an image of the radiation absorption of a cross-sectional area of a subject under examination. An example of an analog system is in U.S. patent application Ser. No. 795,238 filed May 9, 1977 wherein a substantially flat beam of penetrating radiation, such as X-rays, is used to form an image of the radiation absorption of a cross-sectional area, as determined by said beam, of a subject by establishing a relative rotation between said subject and an assembly including a source for producing said penetrating radiation and a detector device having a substantially continuous detector surface having a width dimensioned to permit the detection of the radiation absorption of at least one half of said cross-sectional area, and which detector device is coupled to control means whereby a collection of successive analog primary signal profiles each of which corresponding to the radiation absorption of said subject as a result of successive positions taken by said assembly relative to said subject are stored in an annular region of a memory device (such as a persistent cathode ray tube screen) along a corresponding collection of circularly-shaped primary path trajectories the center of which are located on a circle concentric with said annular region.

It is generally known in the art that in order to eliminate the disturbing effect of the so-called point-spread function on the ultimate tomogram as will be obtained by superposition of the back-projected signal profiles, the original signal profiles in question are to be "pre-processed", which implies, inter alia, that the signal profile information is transformed in accordance with an appropriate spatial filter function. In computerized tomographic systems such filtering process is carried out as an integral part of the data processing program on a sub-routine basis. In analog tomography, however, analog instead of digital techniques have to be employed.

U.S. patent application Ser. No. 755,790 filed Dec. 30, 1976 (now U.S. Pat. No. 4,097,898) discloses proposals for transforming, in accordance with such a spatial filter function which can be described mathematically as a deconvolution function, image information, which is converted via an image intensifier into image information moving in a plane. To this end, this moving image information is swept, so to speak, along a stationary mask having a light transmission characteristic formed in accordance with the desired deconvolution function.

In order to be able, in signal processing for tomographic purposes, to employ one and the same position-independent devoncolution function for all the elements of a cross-sectional area of a subject, that is to be reconstructed into the ultimate tomogram, in principle it is necessary that the area in question be irradiated from a plurality of directions by a substantially flat beam of parallel rays. This holds true for computerized and analog tomography as well. In computerized tomography, signal profile information representative of parallel beams can be obtained by re-arranging and selecting profile elements in an appropriate manner. In analog tomography, however, basically different techniques have to be applied in order to achieve the so-called "parallel" profiles.

U.S. patent application Ser. No. 814,989 filed July 12, 1977 discloses, with a view to analog tomography, proposals for converting signal profiles obtained by successively irradiating a cross-sectional area of a subject by means of an out-fanning (diverging) beam of penetrating radiation from a plurality of different directions, into corresponding continuous signal profiles that may be regarded as being formed by an imaginary beam of parallel rays successively irradiating the respective cross-sectional area from a plurality of different directions. To this end, in accordance with these prior proposals a collection of primary continuous signal profiles recorded in analog form in a memory device and along a predetermined path is read out along a different path so that the divergence of the rays is corrected. The signals resulting from such a read-out operation are representative of the desired "paralleled" signal profiles.

It is an object of the subject invention to provide a signal processing system for analog tomography purposes, in which the two operations mentioned above, i.e., spatial filtering (deconvolution) and "parallelization", are carried out simultaneously.

More particularly, it is an object of this invention to provide a simple, efficient and cost saving arrangement for such a signal processing system.

To achieve these objects, a system according to the subject invention comprises control means of the type as proposed in the afore-mentioned U.S. patent application Ser. No. 814,989 whereby in an analog form the collection of continuous primary signal profiles is stored in a memory device; path trajectory determining means for defining a succession of arc-shaped secondary paths across said collection of recorded signal profiles, each one of said secondary paths covering primary signal profile fragments representative of rays of radiation having the same direction; optical means for providing a spatial filter function; drive means which under control of said path trajectory determining means cause a relative movement between said spatial filter function and said memory device along said succession of secondary paths to occur, whereby primary signal profile fragments such as located along such a secondary path are successively processed with said filter function and are read out; and a detector device for converting the primary signal profile fragments thus processed and read out for each one of said secondary paths into a corresponding sequence of electric signals in the time domain.

In a preferred embodiment of the invention said memory device comprises a storage surface for displaying said primary signal profiles as an optical image of a collection of arc-shaped image lines, said path trajectory determining means including a mask disc disposed opposite to said storage surface and having a light transmitting annular window containing an optical filter the transmission density of which is varying in one dimemsion in accordance with the desired spatial filter function, and an opto-electric detector device being mounted opposite said window for receiving a light information transmitted through this window and which information is indicative of paralleled and processed (deconvoluted) signal profile information.

The invention will be described in greater detail hereinafter with reference to a preferred embodiment. Self-evidently, the invention is not restricted to this preferred embodiment; numerous different embodiments based on the principle of the present invention may be realized.

BRIEF DESCRIPTION OF THE DRAWINGS

As indicated in the above prior U.S. patent application Ser. No. 814,989, it is possible to record a collection of primary signal profiles $p_\alpha$ in a memory device such as screen of a cathode ray tube in the manner shown in FIG. 1. These signal profiles are recorded in the form of arc-shaped segments each having a radius $R_1$ and a centre of curvature $\alpha'$ on a circle having a radius $R_2$ and a centre O. The starting points of the "half" primary signal profiles thus-recorded are located on a circle having a radius $R_3$ and the same centre O. For signal profile $p_\alpha$ such a beginning is indicated by A' while the end point of this half signal profile is indicated by A". These end points are located on a circle having a radius $R_4$ and again the same centre O. The magnitude of this radius $R_4$ and hence the arc length of the half signal profiles is determined by the angle $\phi$ of the substantially flat out-fanning beam of penetrating radiation with which the subject is irradiated. As further indicated in the above prior U.S. patent application, the divergence of the beam of radiation can be corrected when the collection of primary signal profiles is read out in accordance with likewise arc-shaped secondary paths. FIG. 1 shows such a secondary path A'B having a centre of curvature M on a circle with radius $R_1$ and centre O, while the radius of curvature of this secondary path is repesented by $R_2$. The centre of curvature M is related to the position angle $\alpha$ taken by the source of radiation with respect to the subject for achieving the primary signal profile A'A".

Figure 1:
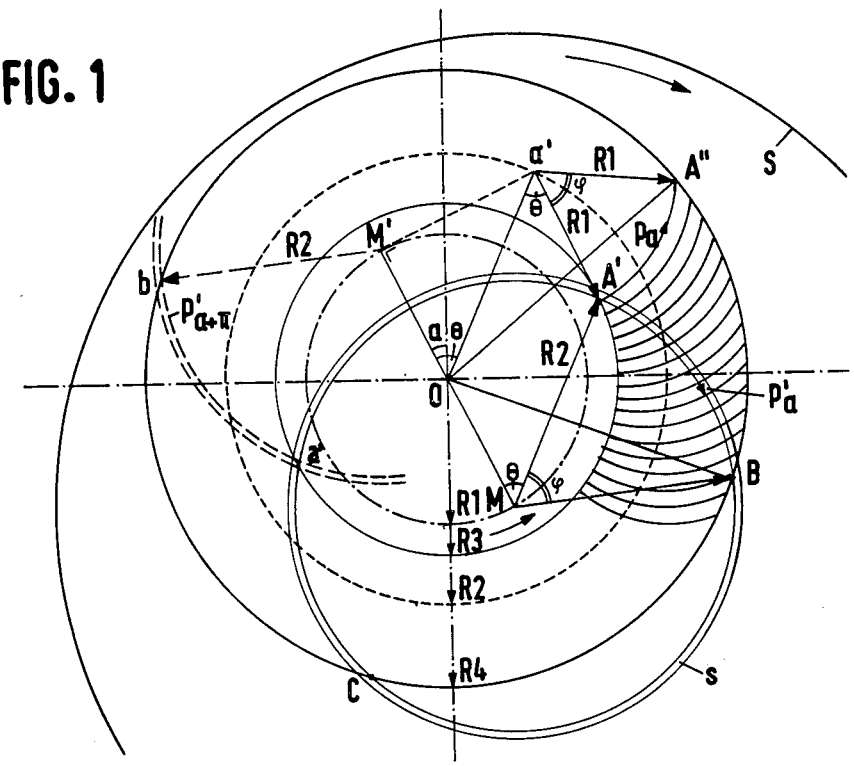
FIG. 1 shows a collection of signal profiles on the screen of a cathode ray tube, in accordance with the instant invention.

Applying the rules of geometry, it can simply be seen that for the above angle of divergence $\phi$ it is obtained that angle A'$\alpha$'A"=angle A'MB. In other words, the arc angles $\phi$ of the half profiles $p_\alpha$ and of the secondary paths are equal.

In accordance with the principle of the present invention, an optical image is formed of the collection of primary half signal profiles, which optical image is in the form of arc-shaped image lines in the preferred embodiment under consideration. An arc-shaped path trajectory such as A'B is projected across these image lines by mounting opposite this optical image a light transmitting annular window having a radius of curvature $R_2$ and a centre of curvature M, at any rate when it is assumed that the projection is performed on a 1:1 basis. The light pattern corresponding to section A'B of the optical image as transmitted by this window corresponds to a "paralleled" profile $p'_\alpha$. In accordance with the invention, all the primary signal profile fragments located along such an arc A'B are successively subjected to the desired deconvolution function, which may be achieved as the transmission characteristic of the window, which is formed in accordance with the desired deconvolution function, is swept, so to speak, along the primary signal profile fragments. This can be realized by rotating a mask including the respective annular window about centre M, as a result whereof a detector receiving the light transmitted by the window receives a signal as a function of the time, which signal corresponds with a deconvoluted and paralleled profile $p''_\alpha$. Furthermore it should be ensured that this centre M of the rotating mask disc S follows the circle having radius $R_2$ and centre O in order to obtain a complete collection of deconvoluted and paralleled profiles $\Sigma p''_\alpha$.

As stated earlier, "half" profiles $p'_\alpha$ are achieved corresponding with a half cross-sectional lamina of the subject as limited by the axis of rotation O (relative rotation of subject and source of radiation). The other half of the lamina of the subject for a parallel beam from the same direction $\alpha$ is achieved $\pi$ radians further on as the "half" profile $p'_{\alpha+\pi}$ in the form of an arc-shaped path a'b likewise having a radius of curvature $R_2$ and having a centre of curvature M' diametrically opposite to centre of curvature M on the circle having radius $R_1$. In order to ultimately achieve the deconvoluted profile of the complete lamina of the subject, consequently, it should be ensured that each time the deconvolution results of associated "half" profiles $p'_\alpha$ and $p'_{\alpha+\pi}$ are combined bearing in mind that the two associated deconvolution results $p''_\alpha$ and $p''_{\alpha+\pi}$ become available sequentially with a time difference corresponding to an angle of rotation $\pi$ of the detector device. Thus the deconvolution result of the first "half" profile must be stored in a memory, to which the deconvolution result of the associated second "half" profile can be added after it has become available. Such a memory may include a memory tube in which the image reconstruction is realized by successive back projection, such as described in e.g. U.S. patent application Ser. No. 795,238, or an auxiliary memory.

For obtaining a result after combining the deconvoluted "half" profiles that corresponds with the deconvolution result of a complete profile, prior to its deconvolution each "half" profile should be supplemented by an empty section so as to form a complete profile, which empty section corresponds to the section contributed to the complete profile by the associated other "half" profile of $\pi$ radians further on. "Half" profiles span an arc $R_2\phi$, supplemented "half" profiles span an arc $2R_2\phi$, deconvoluted (supplemented) "half" profiles likewise span ar arc $2R_2\phi$, so that for receiving a paralleled and deconvoluted (supplemented) "half" profile the detector device should be operative during a period of time corresponding to the traversal of a window arc of $2R_2\phi$ radians, while the deconvolution function on the mask disc should span a window arc of $3R_2\phi$ radians, as elucidated in FIG. 2.

Figure 2:
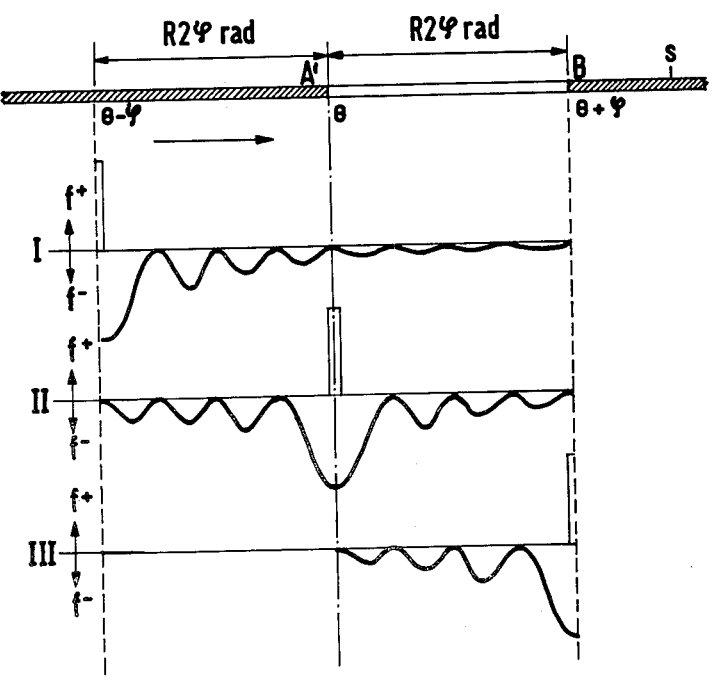
FIG. 2 is a phase diagram indicative of deconvolution of various profiles in accordance with the instant invention.

Phase I of FIG. 2 shows the situation at the point of time of determining the first element of the deconvoluted (supplemented) "half" profile. During the period of time from phase I to phase II only contributions to the deconvolution result are achieved that are caused by the operation of the negative deconvolution function f—. At the point of time of phase II the positive deconvolution function f+ becomes operative for the first time, and at the point of time of phase III the last element of the deconvoluted (supplemented) "half" profile is determined.

As shown in the above, the complete deconvolution of a half profile $p'_\alpha$ by means of a given function requires a window arc of the annular window s in the mask disc S or $3R_2\phi$ radians. Consequently, an appropriate choice of the divergence angle $\phi$ renders it possible to provide a whole number (n) of transmission characteristics along the entire circumference of this window s, each of these transmission characteristics spanning a window arc of $3R_2\phi$. It applies that $3n\phi=2\pi$, which means that $n=2\pi/3\phi=120°/\phi$. During one complete revolution of the mask disc S and hence the annular window s, n half profiles $p'_\alpha$ can be successively processed. Self-evidently, provisions should be made to ensure that the centre of curvature M is moved along the circle having radius $R_1$ a distance depending on the width of the profile and the width of the window s.

As observed above with reference to FIG. 2, a complete deconvolution of a given profile requires each element thereof to be multiplied by a positive f+ as well as a negative f− deconvolution function. Therefore, in principle each one of the profiles to be deconvoluted, especially each element thereof, should be multiplied by these two functions. Starting from an optical image of the half primary signal profiles $p'_\alpha$, two mask discs $S_1$ and $S_2$ are required, for example, the disc $S_1$ providing the positive deconvolution function and the disc $S_2$ providing the negative deconvolution function. By means of a beam splitter as described, for example, in the above prior U.S. patent application Ser. No. 795,238, each of the annular path trajectories as defined by these discs $S_1$ and $S_2$ can be projected across this optical image, so that the collection of half signal profiles $p_\alpha$ can coact with the window s of disc $S_1$ as well as with the window s of disc $S_2$.

An arrangement based on such an organization is rather complicated not only on account of the necessity to employ two mask discs $S_1$ and $S_2$ with associated optical means, but also on account of the fact that these discs $S_1$ and $S_2$ should rotate isochronally, which also applies to the movements of the centres of rotation of these discs along circular paths.

The desired transmission characteristic corresponding with the negative deconvolution function can be realized in different manners, for example by modulating the transmission density of the respective window, which window is in the form of a photographic layer, or by modulating the contour of this material. Self-evidently, the transmission characteristic corresponding with the positive deconvolution function can be realized as a narrow light transmitting slot. As by means of such a positive deconvolution function it is possible to mark the beginning of each new profile, the beginning of the response to $p'_\alpha \cdot f+$ may be used as the synchronizing signal in the further processing of the signals supplied by the detector device, which device receives the light radiation transmitted by the window.

Figure 3:
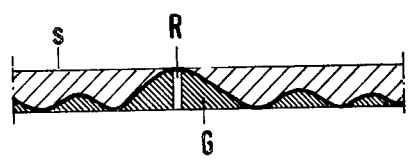
FIG. 3 is a schematic diagram of the modulation of the contour of the window of a mask disc, in accordance with the instant invention.

The above drawback inherent in the use of two mask discs, such as $S_1$ and $S_2$, for achieving a complete deconvolution, may be eliminated by using a single mask disc in which the two required deconvolution functions f− and f+ are integrated. This is possible as the positive deconvolution function f+ is a delta-function. To this end, for example, the contour of the window of mask disc S can be modulated as schematically shown in FIG. 3, the slot associated with f+ transmitting red light (R) and the rest of the mask profile associated with f− providing a complementary color, in this case green (G). By providing each of two detector devices mounted opposite such a window with a red filter and a green filter, respectively signals $\Sigma R \cdot p'_\alpha$ and $\Sigma G \cdot p'_\alpha$ are received. It is readily clear that the positively deconvoluted signal $\Sigma p'_\alpha \cdot f+$ corresponds with $\Sigma R \cdot p'_\alpha$, while the negatively deconvoluted signal $\Sigma p'_\alpha \cdot f-$ corresponds with $\Sigma(R+G)p'_\alpha$.

Instead of employing such color filters, it is possible to pass the "R"-signal through a glass fibre optics arrangement to a separate detector, while the "G"-signal is directly applied to the main detector.

The ultimately achieved collection of paralleled and deconvoluted profiles may either be reproduced in analog form on a cathode ray tube as the ultimate tomogram by means of back projection, as described for example in the above prior U.S. patent application Ser. No. 795,238, or be processed in digital form in a computer.

Figure 4:
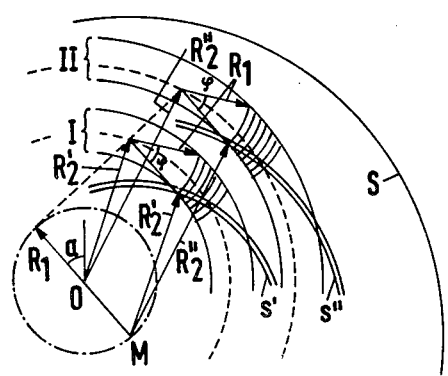
FIG. 4 shows two separate collections of primary "half" profiles in accordance with the instant invention.

If, as also described in the above prior U.S. patent application Ser. No. 814,989, two separate collections I and II (FIG. 4) of primary "half" profiles are recorded, these two collections relating, for example, to two different superimposed laminas of the subject which are concurrently irradiated at the same divergence angle, by means of single mask disc S having two concentric annular windows s' and s" a corresponding pair of paralleled and deconvoluted collections of signal profiles can be obtained. Self-evidently, each window should have an associated detector device, while it is further imperative that profile collections I and II can be recorded in concentric, non-overlapping annular bands.

Figure 5:
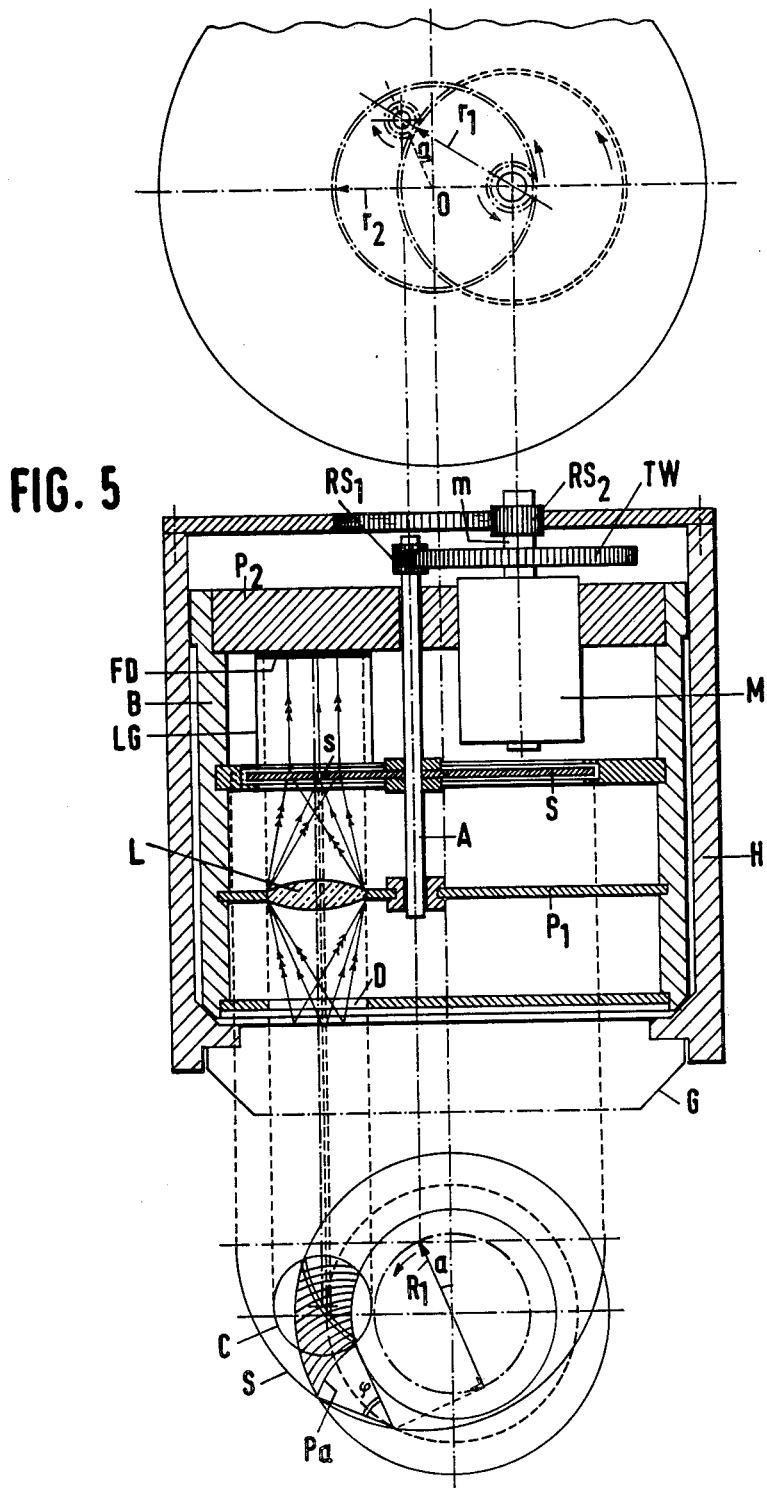
FIG. 5 shows a schematic diagram of an embodiment for paralleling and deconvoluting primary "half" signal profiles in accordance with the instant invention.

FIG. 5 shows a schematic diagram of an embodiment for paralleling and deconvoluting primary "half" signal profiles initially recorded in accordance with arc-shaped image lines. The memory tube G serving this purpose is fixedly mounted with its viewing screen facing upwards in a cylindrical housing H, in which a sleeve B is mounted for coaxial rotation. A bottom plate D having a circular diaphragm eccentrically mounted therein, the circumference of which is indicated by circle C, is fixedly mounted in sleeve B. This diaphragm C passes only the corresponding portion of the collection of primary profiles $p_\alpha$ recorded in the memory tube to a first optical system. For the sake of simplicity, in FIG. 5 this optical system is shown as a single lens L having a transmission ratio of 1:1, which lens is eccentrically mounted in a support plate $P_1$. A cover plate $P_2$ is fixedly mounted in the sleeve B, which plate $P_2$ serves as a support for a drive motor M. A shaft A with a pinion $RS_1$ having diameter $2r_a$ is mounted for rotation in plates $P_1$ and $P_2$ and has fixedly secured thereto a mask disc S having an annular window s with a transmission characteristic as prescribed by the desired deconvolution. A planar photosensitive detector device FD is mounted on plate $P_2$, which detector device is arranged to receive by means of a light guiding path LG, which may be a fibre bundle of sufficient cross-sectional area, the total flux of the light passed by the annular windows s. Via an appropriate transmission mechanism, the motor M is coupled in driving relationship with the shaft A, so that a rotation of the output shaft m of this motor having pinion $RS_2$ with diameter $2r_m$ results not only in a rotation of the mask disc S, but also in a rotation of the sleeve B, the shaft A traversing a circle having radius $R_1$ and centre O. The number of revolutions $N_S$ of the mask disc S is determined by the ratio $r_a/r_1$, in which $r_1$ is the radius of a gear wheel TW fixedly secured to the motor shaft, which gear wheel is adapted to engage the pinion $RS_1$ on shaft A. The motor shaft is further fixedly secured to the pinion RS$_2$ having radius r$_m$ and adapted to engage an internal gear having radius r$_2$. Hence the number of revolutions N$_M$ at which shaft A transverses the circle having radius R$_1$ is determined by the ratio r$_2$/r$_m$. In this manner, the two rotations, i.e. the relatively rapid rotation of the mask disc S about its centre and the relatively slow rotation of shaft A about centre O, can be concurrently realized by motor M. The internal gear having radius r$_2$ is formed in a cover plate DP attached to the housing H.

Assuming that a total number p of primary "half" signal profiles p$_\alpha$ is recorded in memory device G over an angle of 2$\pi$ radians and that the time required for reading out these p profiles over 2$\pi$ radians is t, it applies that the time t$_p$ required for reading out a profile is defined by t$_p$=t/p. In the event of a divergence angle of $\phi$ radians, a number n of deconvolution windows are provided along the circumference of the annular window s, in which n=$\pi$/3$\phi$. During the above period of time of t$_p$ seconds the mask disc S rotates through an angle of 3$\alpha$ radians, the speed of rotation of the mask disc S relative to the centre of curvature M being determined by $\omega$S=3$\phi$/t$_p$=3$\phi$p/t radians/second. In this period of time of t$_p$ seconds the shaft A should rotate through an angle of 2$\pi$/p radians along the circle having radius R$_1$ and centre O. The speed at which shaft A rotates about this centre O is therefore determined by $\omega$M=(2$\pi$/p)/(t/p)=2$\pi$/t radians/second. When these two rotations are taken from the same motor shaft rotating at an angular velocity $\omega_m$=2$\pi$T, in which T is the number of revolutions of the motor shaft per second, it applies that N$_M\pi_M$=$\omega_m$=N$_S\omega_S$. This means that N$_M$2$\pi$/t=2$\pi$T=N$_S$3$\phi$p/t, so that the choice must be N$_M$=T·t; N$_S$=2$\pi$tT/3$\phi$p=2$\pi$N$_M$/3$\phi$p. Assuming, for example, that t=1 second; p=720; $\phi$=20°=2$\pi$/18 radians, and T=10 revolutions/second, it applies that N$_M$=10=r$_2$/r$_m$ and N$_S$=2$\pi$·10·18/2$\pi$·720·3=1/12- =r$_a$/r$_1$.

In this embodiment it is assumed that the two deconvolution functions f+ and f− required for a complete deconvolution have been integrated in the window s of a single mask disc S in the manner described above.

The power required for energizing the motor, as well as the signals derived from the photosensitive detector, may be supplied and discharged via the shaft extending through O by means of, for example, slip rings.

I claim:

1. A signal processing system for use in an analog tomographic system in which successive primary absorption profile signals are produced from a flat diverging beam of penetrating radiation directed through at least one half of a cross-sectional slice of a subject during corresponding successive relative angular positions between the subject and an assembly including detector means and a source for the beam of penetrating radiation, said system comprising memory and display means having an annular region disposed about a memory center for storing and displaying a succession of primary signal profiles corresponding to said successive primary absorption profile signals, said memory and display means storing and displaying said primary signal profiles along segments of corresponding primary trajectories extending radially from the memory center and crossing the annular region, said primary trajectory segments being circular arcs generated about successive primary trajectory centers which are positioned in a primary trajectory circle concentric with the annular region, a rotatable optical filter having an axis of rotation and at least one spacial filtering region spaced from the axis of rotation, rotating and orbiting means mounting said optical filter over said memory display means for orbiting the axis of rotation of the optical filter in a secondary trajectory circle concentric with the memory center and for rotating the optical filter about its axis of rotation to sweep said spacial filtering region through secondary trajectory segments across the annular region to transmit successive series of fragments of corresponding successive series of primary signal profiles through the spacial filtering region, said optical filter and said rotating and orbiting means being designed so that said transmitted fragments of primary signal profiles in each series correspond to parallel portions of a series of the diverging beams of penetrating radiation from which the corresponding series of primary signal profiles was generated, and a detector device responsive to the transmitted fragments of primary signal profiles for generating successive secondary profile signals.

2. A signal processing system as claimed in claim 1 including an optical system mounted by said rotating and orbiting means for movement with said optical filter for transmitting light from said memory and display means to said optical filter.

3. A system according to claim 1 wherein said memory and display means includes an electronic memory tube.

4. A system according to claim 1 wherein the divergence angle of the beam of penetrating radiation is selected so that the transmission characteristic corresponding with the deconvolution of a signal profile is provided a whole number of times along the circumference of the optical filter.

5. A system according to claim 1 wherein the light transmissivity of said transmitting region as considered along the circumference of the optical filter, varies in accordance with the desired deconvolution function.

6. A system according to claim 1 wherein the contour of said transmitting region as considered along the circumference of the optical filter, varies in the direction of light transmission in accordance with the desired deconvolution function.

* * * * *